(12) United States Patent
Yamka et al.

(10) Patent No.: US 9,554,584 B2
(45) Date of Patent: *Jan. 31, 2017

(54) COMPOSITIONS AND METHODS FOR CONTROLLING THE WEIGHT OF ANIMALS

(71) Applicant: Hill's Pet Nutrition, Inc., Topeka, KS (US)

(72) Inventors: Ryan Michael Yamka, Succasunna, NJ (US); Kim Gene Friesen, Carthage, IN (US)

(73) Assignee: Hill's Pet Nutrition, Inc., Topeka, NY (US)

( * ) Notice: Subject to any disclaimer, the term of this patent is extended or adjusted under 35 U.S.C. 154(b) by 248 days.

This patent is subject to a terminal disclaimer.

(21) Appl. No.: 14/069,714

(22) Filed: Nov. 1, 2013

(65) Prior Publication Data
US 2014/0057017 A1 Feb. 27, 2014

Related U.S. Application Data

(62) Division of application No. 12/528,373, filed as application No. PCT/US2007/062710 on Feb. 23, 2007, now Pat. No. 8,597,677.

(51) Int. Cl.
*A23K 20/142* (2016.01)
*A23K 1/16* (2006.01)

(52) U.S. Cl.
CPC ........... *A23K 1/1634* (2013.01); *A23K 20/105* (2016.05); *A23K 20/142* (2016.05); *A23K 20/147* (2016.05); *A23K 20/30* (2016.05); *A23K 50/40* (2016.05); *A23V 2002/00* (2013.01)

(58) Field of Classification Search
None
See application file for complete search history.

(56) References Cited

U.S. PATENT DOCUMENTS

| | | |
|---|---|---|
| 5,273,754 A | 12/1993 | Mann |
| 6,042,857 A * | 3/2000 | Jones et al. ............... 426/106 |
| 6,517,877 B2 | 2/2003 | Gannon |
| 2003/0224496 A1 | 12/2003 | Jakel et al. |
| 2004/0081743 A1 | 4/2004 | Laflamme |
| 2004/0208979 A1 | 10/2004 | Miller et al. |
| 2006/0073192 A1 | 4/2006 | Friesen et al. |
| 2006/0141011 A1 | 6/2006 | Jewell |
| 2006/0280776 A1 | 12/2006 | Koide |

FOREIGN PATENT DOCUMENTS

| | | |
|---|---|---|
| EP | 0986961 | 3/2000 |
| GB | 1310232 | 3/1973 |
| JP | S59-91850 A | 5/1984 |
| JP | H03-219838 A | 9/1991 |
| JP | 2005-521426 A | 7/2005 |
| JP | 2006-510711 A | 3/2006 |
| WO | WO 98/01042 | 1/1998 |
| WO | WO 2007/051134 | 5/2007 |

OTHER PUBLICATIONS

Coffey, Richard D., et al., ASC-147: Feeding Growing-Finishing Pigs to Maximize Lean Growth Rate, (Apr. 15, 2005), pp. 1-6.*
Rolls, Barbara J., et al, Am J Clin Nutr, 76 (2002) pp. 1207-1213.*
AAFCO, 2006, Association of American Feed Control Officials, 2006 Official Publication, pp. 160-065.
D. N. Salter "Lysine requirements and whole-body protein turnover in growing pigs", British Journal of Nutrition (1990), 63, 503-513.
Dzanis, D.A. "The Association of American Feed Control Officials Dog and Cat Food Nutrient Profiles: Substantiation of Nutritional Adequacy of Complete and Balanced Pet Foods in the United States," Journal of Nutrition, (1994) pp. 2535S-2539S, 124:I2 Wistar Institute of Anatomy and Biology, Philadelphia, PA., US. DXP008067009.
Gaylord, T. Gibson et al., The modification of Poultry by-product meal for use in hybrid striped Bass Morone chrysops X M. saxatilis Diets, Journal of the Word Aquaculture Society, (Sep. 2005) vol. 36, No. 3, pp. 363-374.
Hand et al., eds., 1983, "Obesity," Chapter 13 in: *Small Animal Clinical Nutrition*, 4th ed., pp. 401-430.
Hill's Pet Nutrition Canada, Inc., 2008, Update on Evidence-Based Clinical Nutrition Technical Information Services.
International Search Report and Written Opinion in International Application No. PCT/US07/062710, mailed Oct. 16, 2007.
J. W. Smith, 2nd, "Effects of dietary energy density and lysine:calorie ratio on growth performance carcass characteristics of growing-finishing pigs" J Anim Sci 1999. 77:3007-3015.
Jewell, Dennis E., Satiety Reduces Adiposity in Dogs, Veterinary Therapeutics (Winter 2000), vol. 1, No. 1, pp. 17-23.

(Continued)

*Primary Examiner* — Brian-Yong Kwon
*Assistant Examiner* — Lyndsey Beckhardt

(57) ABSTRACT

Compositions are provided comprising a balance between lysine and essential amino acids and metabolizable energy. The compositions are useful in methods to prevent or treat obesity in an animal without concomitant loss of lean muscle mass. The compositions may also be used in methods to preserve or to cause a gain in lean muscle mass in an animal in need thereof.

23 Claims, No Drawings

(56) References Cited

OTHER PUBLICATIONS

Parvin et al., 1977, "Microdetermination of (-)carnitine and carnitine acetyltransferase activity," Analytical Biochem. 79(1-2):190-201.
Royal Canin Medi-Cal, undated, "Satiety Support: Formulated for weight loss," Product Information.
Williams et al., 2001, "Effects of dietary protein on whole-body protein turnover and endocrine function in young-adult and aging dogs," J. Animal Science 79(12):3128-3136.
www.hillsvet.com, Canine r/d Product Information, http://www.hillsvet.com website, Retrieved Dec. 6, 2008.
www.medi-cal.ca, Satiety Support Product Information: Summary, Features, Ingredients and Composition, http://www.medi-cal.ca/diets/diets.php?diet=44&page=summary&lang=en, Retrieved Dec. 6, 2008.
Yamka et al., 2006, "Identification of Canine Markers Related to Obesity and the Effects of Weight Loss on the Markers of Interest," Intern. J. Appl. Res. Vet. Med. 4(4):282-292.
Yamka et al., 2007, "Effects of 3 Canine Weight Loss Foods on Body Composition and Obesity Markers," Intern. J. Appl. Res. Vet. Med. 5(3):125-132.
Yamka et al., 2008, "Canine Weight Loss Study—Synopsis," Clinical Evidence Report, Hill's Technical Information Services.

\* cited by examiner

COMPOSITIONS AND METHODS FOR CONTROLLING THE WEIGHT OF ANIMALS

This application is a divisional of U.S. patent application Ser. No. 12/528,373, filed Aug. 24, 2009, now U.S. Pat. No. 8,597,677, which is a 371 entry of International Application No. PCT/US2007/062710 filed Feb. 23, 2007.

FIELD OF THE INVENTION

This invention relates to compositions and methods for controlling the weight of animals.

BACKGROUND OF THE INVENTION

Animals, particularly companion animals (e.g., dogs and cats), may weigh more than their ideal body weight. Having an excess of adipose tissue, these animals may be clinically diagnosed as, e.g., "fat", "overweight", or "obese" and, as such, are more likely to suffer from associated physical disorders such as arthritis, heart disease, respiratory disease, diabetes, bladder cancer, hypothyroidism, joint disease and/or pancreatitis.

Attempts to prevent or reduce the amount of excess adipose tissue on companion animals typically include dietary restriction and exercise. Indeed, many "low" or "reduced" calorie foods for overweight companion animals have been developed and are commercially available for the control of calorie intake, prevention of weight gain or for the promotion of weight loss. One strategy in weight loss involves high protein diets with high protein to calorie ratios in order to reduce the amount of body fat in humans. A similar approach has been used in companion animal products (e.g. PRESCRIPTION DIET® FELINE M/D®, Hill's Pet Nutrition, Topeka, Kans.). High protein diets have proven to be effective in weight loss in cats; however high protein foods have had mixed results when applied to canine weight management programs. Treatment strategies also include increasing the fiber and/or protein content while reducing the fat in the food. Depending on the fiber source, the fiber can induce satiety via gut distention or through feedback mechanisms GLP-1). Fiber can be effective in reducing the digestibility of food resulting in a lower availability of high calorie nutrient components (i.e. fat and carbohydrates).

Despite the availability of such pet food formulations, however, the need remains for the development of additional formulations comprising innovative ingredients and nutrients for preventing or treating obesity in companion animals. For example, one problem with weight loss is that lean muscle mass is commonly lost as a component of total body weight loss even though it is not the target tissue. Thus, there is a need for compositions which can cause weight loss in animals without causing loss of lean muscle mass.

We have now surprisingly discovered that a weight loss composition formulated to include a specific balance of essential and limiting amino acids can cause weight loss that is characterized by a preservation or gain of lean muscle. Thus, as contemplated herein, the compositions of the present invention may be useful to prevent or treat obesity in an animal without the concomitant loss of lean muscle in the animal.

Essential amino acids are amino acids that cannot be synthesized de novo, or in sufficient quantities by an organism and thus must be supplied in the diet. Essential amino acids vary from species to species, depending upon the organism's metabolism. For example, it is generally understood that the essential amino acids for dogs and cats (and humans) are phenylalanine, leucine, methionine, lysine, isoleucine, valine, threonine, tryptophan, histidine and arginine, in addition, taurine, while technically not an amino acid but a derivative of cysteine, is an essential nutrient for cats. A balanced diet can provide all the essential amino acids, however, there are certain essential amino acids that are more critical, as a diet deficient in one of them will limit the usefulness of the others, even if the other essential amino acids are present in sufficient quantities. Generally, these limiting amino acids are methionine, cysteine, tryptophan, and lysine.

SUMMARY OF THE INVENTION

We have identified the positive effects of balancing essential amino acids in weight loss compositions. Specifically, this includes balancing, the quantity of lysine to leucine, methionine, methionine+cysteine, and/or phenylalanine+tyrosine. Particularly, the formulations of the present invention relate to compositions that are useful to prevent and treat obesity in an animal, and preserve and cause lean muscle gain in an animal in one embodiment, the composition is a pet food. In another embodiment, the composition is a wet pet food. In still another embodiment, the composition is a dry pet food.

In accordance with the present invention. Composition 1.0 is provided comprising.

about 1.4 to about 2.1% lysine, wherein the composition has a leucine to lysine ratio of about 1.7 to about 2.7, methionine+cysteine to lysine ratio of about 0.5 to about 1.5, a phenylalanine+tyrosine to lysine ratio of about 1.3 to about 2.1, and about 4 to about 8 grams of lysine per Mcal.

Additional compositions of the present invention may comprise any of the following:

1.1. Composition 1 further comprising about 20 to about 30%, about 22 to about 28%, or about 24 to about 26% dietary fiber;

1.2. Compositions 1 or 1.1 further comprising about 8 to about 14%, about 9 to about 13%, about 10 to about 12%, or about 10.3% to about 11.6% crude fiber;

1.3. Any of the preceding compositions further comprising about 1.2 to about 4.0%, about 1.3 to about 3.6%, about 1.4 to about 3.3%, about 1.5 to about 3.1%, about 3.0%, or about 1.6% soluble fiber;

1.4. Any of the preceding compositions comprising about 4 to about 7, about 4.2 to about 6.8, about 4.7 to about 5.8, or about 5.0 to about 5.6 grams of lysine per Mcal;

1.5. Any of the preceding compositions comprising about 1.5% to about 1.9% lysine, about 1.6% to about 1.8% lysine, or about 1.7% lysine;

1.6. Any of the preceding compositions comprising a leucine to lysine ratio of about 2.0 to about 2.4, about 2.1 to about 2.3, or about 2.2;

1.7. Any of the preceding compositions comprising a methionine+cysteine to lysine ratio of about 0.8 to about 1.2, about 0.86 to about 1.1, about 0.90 to about 1.0, or about 0.95 to about 0.98;

1.8. Any of the preceding compositions comprising a phenylalanine+tyrosine to lysine ratio of about 1.5 to about 1.9, about 1.6 to about 1.8, or about 1.6 to about 1.7;

1.9. Any of the preceding compositions comprising a tryptophan to lysine ratio of about 0.1 to about 0.2, about 0.12 to about 0.18, about 0.13 to about 0.17, or about 0.14 to about 0.16;

1.10. Any of the preceding compositions comprising a threonine to lysine ratio of about 0.5 to about 0.9, about 0.6 to about 0.8, or about 0.7;

1.11. Any of the preceding compositions comprising an arginine to lysine ratio of about 0.75 to about 1.2, about 0.85 to about 1.1, preferably about 0.89 to about 1.1, or about 0.94 to about 1.0.

1.12. Any of the preceding compositions comprising an isoleucine to lysine ratio of about 0.51 to about 0.82, about 0.58 to about 0.74, about 0.61 to about 0.71, about 0.68, or about 0.64;

1.13. Any of the preceding compositions comprising a valine to lysine ratio about 0.6 to about 1.0, about 0.7 to about 0.9, about 0.7 to about 0.8, or about 0.76 to about 0.80;

1.14. Any of the preceding compositions comprising a histidine to lysine ratio about 0.3 to about 0.5, about 0.35 to about 0.44, about 0.37 to about 0.41, or about 0.40;

1.15. Any of the preceding compositions comprising a methionine to lysine ratio of about 0.5 to about 0.9, about 0.6 to about 0.8, about 0.67 to about 0.76, or about 0.70 to about 0.73;

1.16. Any of the preceding compositions comprising a metabolizable energy content of about 2600 to about 3950 Kcal/kg; about 2900 to about 3610 Kcal/kg; about 3080 to about 3450 Kcal/kg; or about 3240 to about 3280 Kcal/kg;

1.17. Any of the preceding compositions comprising about 75 to about 200 ppm, or about 100 to about 150 ppm manganese;

1.18. Any of the preceding compositions comprising about 200 to about 500 ppm, about 250 to about 400 ppm, or about 300 to about 350 ppm L-carnitine;

1.19. Any of the preceding compositions having about 24 to about 41%, or about 28 to about 37% crude protein;

1.20. Any of the preceding compositions comprising about 6.3 to about 11%, or about 7.5 to about 10% fat;

1.21. Any of the preceding compositions comprising about 4.6% to about 7.0%, or about 5.5 to about 6.6% ash;

1.22. Any of the preceding compositions comprising about 27 to about 45%, about 31 to about 39%, or about 33% to about 37% carbohydrate; and 1.23. Any of the preceding compositions being a dry food, or further comprising a moisture content of about 5.3 to about 8.4%, or about 6.3% to about 7.4%.

In another embodiment of the present invention, Composition 2.0 is provided comprising:
about 24 to about 41% crude protein;
about 20 to about 32% dietary fiber;
leucine:lysine ratio of about 2 to about 3;
about 1.2 to about 1.7% methionine; and
about 50 to about 500 ppm manganese; and
about 4.6 to about 6.8 grams of lysine per Mcal.

Additional compositions of the present invention may comprise any of the following:

2.1. Composition 2.0 having about 22 to about 29%, or about 24 to about 27% dietary fiber;

2.2. Composition 2.0 or 2.1 having about 1.2 to about 4.0%, or about 2 to about 3% soluble fiber;

2.3. Any of compositions 2.0-2.2 having about 21 to about 27%, or about 23 to about 25% insoluble fiber;

2.4. Any of compositions 2.0-2.3 wherein the crude protein is about 33 to about 36%, or about 35%;

2.5. Any of compositions 2.0-2.4 having about 5.1 to about 6.3 grams of lysine per Mcal; about 5.4 to about 6.0 grams of lysine per Mcal; or about 5.7 grams of lysine per Mcal.

2.6. Any of compositions 2.0-2.5 having about 1.3% to about 1.6%, or about 1.4 to about 1.5% methionine;

2.7. Any of compositions 2.0-2.6 having about 75 to about 200) ppm manganese; or about 100 to about 150 ppm manganese;

2.8. Any of compositions 2.0-2.7 having about 200 to about 500 ppm carnitine; about 250 to about 400 ppm carnitine; or having about 300 to 350 ppm carnitine;

2.9. Any of compositions 2.0-2.8 having a methionine+cysteine to lysine ratio of about 1:1.25 to about 1.75:1; or a methionine+cysteine to lysine ratio of about 1:1;

2.10. Any of compositions 2.0-2.9 having a leucine to lysine ratio of about 1.4 to about 2.6, about 1.8 to about 2.2, or about 2;

2.11. Any of compositions 2.0-2.10 comprising about 1 to about 10%, about 3 to about 7%, or about 4 to about 6% ash;

2.12. Any of compositions 2.0-2.11 having about 2 to about 13%, about 8 to about 11%, or about 5 to about 7% fat;

2.13. Any of compositions 2.0-2.12 having a metabolizable energy content of about 2000 to about 5000 kcal/kg, about 2480 to about 3720 kcal/kg, about 2800 to about 3400 kcal/kg, or about 3100 kcal/kg.

2.14. Any of compositions 2.0-2.13 being a wet food or having a moisture content of about 70 to about 90%.

2.15. Composition 2.14 having metabolizable energy content of about 720 to about 1080 kcal/kg, about 810 to about 990 kcal/kg, or about 900 kcal/kg on a wet matter basis.

In another aspect, the invention relates to methods to prevent or treat obesity in an animal without concomitant loss of lean muscle mass by administering to said animal any of compositions 1.0-2.15 in an effective amount to prevent or treat obesity in said animal. The compositions may be administered to the animals for an effective amount of time.

In another aspect, the invention relates to a method for the preservation or gain of lean muscle in an animal by administering to the animal an effective amount of any of compositions 1.0-2.15. The compositions may be administered to the animal for an effective amount of time.

The compositions and methods are useful for treating animals, specifically, companion animals, preferably dogs and cats, more preferably, dogs. The animals may be overweight, normal/ideal weight, or underweight.

Additional or alternative advantages and benefits of the present invention will be apparent to one of skill in the art.

DETAILED DESCRIPTION OF THE INVENTION

It is contemplated that the invention described herein is not limited to the particular methodology, protocols, and reagents described as these may vary. It is also to be understood that the terminology used herein is for the purpose of describing particular embodiments only, and is not intended to limit the scope of the present invention in any way.

Unless defined otherwise, all technical and scientific terms used herein have the same meanings as commonly understood by one of ordinary skill in the art to which this invention belongs. All patents, patent applications, publications, and other references cited or referred to herein are incorporated by reference for all purposes.

As used herein and in the appended claims, the singular forms "a", "an", and "the" include plural reference unless the context clearly dictates otherwise.

As used herein, the terms "overweight", "fat", "obese", "obesity" and like terms refer to a body weight condition of an animal that is more than its' ideal weight. For example, the term "fat" as applied to an animal can mean any animal that is determined to have an excess amount of body adipose tissue or an animal that is prone to developing an excess amount of body adipose tissue using techniques and methods known to veterinary care professionals and others of skill in the art. For example, an animal is considered "fat" if (1) the animal has a Body Mass Index (BMI) of 25 or more (a number considered to include "overweight" and "obese" animals in some methods of characterizing animal conditions), (2) the animal's weight is 15% or more than its "ideal" body weight as defined by veterinary care professionals, or as known to one of skill in the art, (3) an animal's percent body fat is 27% or more as determined by dual-energy X-ray absorptiometry ("DEXA"), or (4) an animal has a body condition score ("BCS") of more than 3 on a scale from 1 to 5 as determined by one of skill in the art using the method disclosed in "Small Animal Clinical Nutrition", 4$^{th}$ Edition, in Chapter 13 (ISBN 0-945837-05-4) or its equivalent using other BCS methods. In some cases, animals that are 20% or more over ideal body weight are considered obese.

As used herein, "treatment of obesity" refers to the reduction of body weight of an obese animal until the animal has achieved its ideal body weight, as determined according to conventional methods, e.g., by administering an effective amount of a composition of the present invention to an animal. "Prevention of obesity" refers to preventing an animal from attaining a body weight condition that would be deemed by one of skill in the art as being more than ideal for the animal, e.g., by administering an effective amount of a composition of the present invention to the animal.

As used herein, "an amount effective", "an effective amount", and like terms refer to that amount of a compound, material or composition as described herein that may be effective to achieve a particular biological result. Such results may include, but are not limited to the treatment and/or prevention of obesity and/or the preservation or gain of lean muscle mass. Such effective activity may be achieved, for example, by administration of compositions of the present invention to an animal. An effective amount may be based on several factors, including an animal's ideal weight, the metabolizable energy of the composition, and frequency of feeding the animal compositions of the present invention, e.g., once, twice, or three times daily, and other compositions fed to the animal.

As used herein, an "effective amount of time" may be determined by observing or measuring the weight, weight loss, or lean muscle gain in an animal, and may be determined by one of skill in the art without undue experimentation.

The present invention relates to any animal, preferably a mammal, more preferably a companion animal. The term "companion animal" refers to any animal that lives in close association with humans and includes, but is not limited to, canines and felines of any breed. For example, it is contemplated herein that this term may also encompass any animal whose diet may be controlled by humans and which may benefit from feeding the formulations disclosed herein. These animals may include, for example, domesticated farm animals (e.g. cattle, horses, swine, etc.) as well as undomesticated animals held in captivity, e.g. in zoological parks and the like. Preferably, companion animals are cats and dogs, preferably dogs.

All percentages expressed herein are on a weight by dry matter basis unless specifically stated otherwise.

Without being limited to any theory or particular mode of action, the present invention is based on the surprising discovery that certain compositions can be used to prevent and/or treat obesity while preserving or causing a gain in lean muscle mass by balancing the lysine content of the composition in particular ratios to other amino acids is the composition. Preferably, lysine is balanced to one or more essential amino acids (e.g., phenylalanine, leucine, methionine, isoleucine, valine, threonine, tryptophan, histidine and arginine). More preferably, lysine is balanced to one or more essential amino acids, including one or more limiting amino acids (methionine, cysteine, tryptophan). The lysine ratio may be expressed against one or more amino acids. Balancing the ratio of lysine to metabolizable energy is also important in the present invention.

As contemplated herein, the compositions of the present invention are meant to encompass nutritionally complete and balanced pet food compositions. Nutritionally complete and balanced pet food compositions are familiar to one of skill in the art. For example, nutrients and ingredients such as those disclosed herein as well as others suitable for animal feed compositions, and recommended amounts thereof, may be found, for example, in the Official Publication of the Associate of American Feed Control Officials ("AAFCO"), Inc., *Nutrient Requirements of Dogs and Cats,* 2006.

Protein may be supplied by any of a variety of sources known by those skilled in the art, including plant sources, animal sources, or both. Animal sources include, for example, meat, meat by-products, seafood, dairy, eggs, etc. Meats include, for example, the flesh of poultry, fish, and mammals (e.g., cattle, pigs, sheep, goats, and the like). Meat by-products include, for example, lungs, kidneys, brain, livers, and stomachs and intestines (freed of all or essentially all their contents). The protein can be intact, almost completely hydrolyzed, or partially hydrolyzed. Protein content of foods may be determined by any number of methods known by those of skill in the art, for example, as published by the Association of Official Analytical Chemists in *Official Methods of Analysis* ("OMA"), method 988.05. The amount of "crude protein" in a composition disclosed herein may be determined based on the amount of nitrogen in the composition according to methods familiar to one of skill in the art.

Fat can be supplied by any of a variety of sources known by those skilled in the art, including meat, meat by-products, fish oil, and plants. Plant fat sources include wheat, flaxseed, rye, barley, rice, sorghum, corn, oats, millet, wheat germ, corn germ, soybeans, peanuts, and cottonseed, as well as oils derived from these and other plant fat sources. Fat content of foods may be determined by any number of methods known by those of skill in the art, such as by OMA methods 920.39, 954.02 and 960.39.

Carbohydrate may be supplied by any of a variety of sources known by those skilled in the art, including oat fiber, cellulose, peanut hulls, beet pulp, parboiled rice, corn starch, corn gluten meal, and any combination of those sources. Grains supplying carbohydrate include, but are not limited to, wheat, corn, barley, and rice. Carbohydrate content of foods may be determined by any number of methods known by those of skill in the art. Generally, carbohydrate percentage may be calculated as nitrogen free extract ("NFE"), which may be calculated as follows: NFE=100%−moisture %−protein %−fat %−ash %−crude fiber %.

Dietary fiber refers to components of a plant which are resistant to digestion by an animal's digestive enzymes. Dietary fiber components of foods may be determined by any number of methods known by those of skill in the art, such as OMA method 991.43/32.1.17 (1994). Dietary fiber includes soluble and insoluble fibers.

Soluble fiber are resistant to digestion and absorption in the small intestine and undergo complete or partial fermentation in the large intestine, e.g., beet pulp, guar gum, chicory root, psyllium, pectin, blueberry, cranberry, squash, apples, oats, beans, citrus, barley, or peas. Insoluble fiber may be supplied by any of a variety of sources, including cellulose, whole wheat products, wheat oat, corn bran, flax seed, grapes, celery, green beans, cauliflower, potato skins, fruit skins, vegetable skins, peanut hulls, and soy fiber. Soluble and insoluble fiber content of foods may be determined by any number of methods known by those of skill in the art, preferably OMA method 991.43/32.1.17 (1994).

Crude fiber includes indigestible components contained in cell walls and cell contents of plants such as grains, e.g., hulls of grains such as rice, corn, and beans. Crude fiber content of foods may be determined by any number of methods known by those of skill in the art, such as by OMA 16th edition method 962.09/4.6.01.

The amino acid percentage of the compositions in the present invention may be determined by any means known in the art. For example, the values for the total amount of lysine provided by the invention can be determined using methods known in the art, including OMA methods 975.44, 988.15 and 994.12 (1995). As another example, tryptophan content may be determined according to OMA method 988.15 (1995); methionine, cysteine and other amino acid content may be determined according to OMA method 994.12 (1995). Amino acid content may also be determined according to OMA method 982.30. The essential amino acids in the present compositions may be supplied by any number of sources, including crude protein, or addition of free amino acids to the composition.

Metabolizable energy (ME) of a diet is the energy available to an animal upon consumption of the diet after subtracting the energy excreted in feces, urine, and combustible gases. Metabolizable energy values may be determined by methods known by those skilled in the art, such as detailed in *Association of American Feed Control Officials: Official Publication*, Atlanta, Ga., pages 160-165 (2006).

"Ash" consists of compounds that are not organic or water, generally produced by combustion of biological materials. Ash may be determined by any number of methods known by those of skill in the art, such as OMA method 942.05.

Carnitine, or L-carnitine, is a vitamin-like compound synthesized in the body from lysine and methionine. Carnitine may be naturally present in ingredients of the of the present invention, or carnitine may be added to the compositions. Methods of measuring carnitine are known in the art, such as described in R. Parvin and S. V. Pande, "Microdetermination of (−)Carnitine and Carnitine Acetyltransferases Activity," ANALYTICAL BIOCHEMISTRY, vol. 79, pp. 190-201 (1977).

The compositions of the present invention also contain one or more minerals and/or trace elements, e.g., calcium, phosphorus, sodium, potassium, magnesium, manganese, copper, zinc, choline, or iron salts. One preferred trace element is manganese. Manganese is essential to a host of enzymes as a cofactor, which may regulate the metabolism of foods, including proteins, fats, and carbohydrates. Such enzymes may include oxidoreductases, transferases, hydrolases, lyases, isomerases, ligases, lectins, and integrins. Manganese also affects bone development and neurological function. Manganese may be naturally present in the components of the compositions, or it may be added to compositions. Methods of measuring manganese content in a composition are well known to those of skill in the art, such as OMA 965.17 and 985.01.

The compositions of the present invention may also include vitamins and minerals in amounts required to avoid deficiency and maintain health. These amounts, and methods of measurement are known by those skilled in the art. For example, AAFCO provides recommended amounts of such ingredients for dogs and cats. As contemplated herein, useful vitamins may include, but are not limited to, vitamin A, vitamin $B_1$, vitamin $B_2$, vitamin $B_6$, vitamin $B_{12}$, vitamin C, vitamin D, vitamin E, vitamin H (biotin), vitamin K, folic acid, inositol, niacin, and pantothenic acid.

The compositions of the present invention may additionally comprise additives, stabilizers, fillers, thickeners, flavorants, palatability enhancers and colorants in amounts and combinations familiar to one of skill in the art.

In one embodiment, the compositions are in the form of a food or pet food. In another embodiment, the composition is a treat. Treats are known to those skilled in the art, and can include, for example, compositions that are given to an animal to eat during non-meal time, e.g., a dog biscuit.

While foods of any consistency or moisture content are contemplated, preferably the compositions of the present invention may be, for example, a wet or dry animal food composition. "Wet" food refers to food which has a moisture content of about 70 to about a 90%. "Dry" food refers to compositions with about 5 to about 15% moisture content and is often manufactured in the form of small bits or kibbles. Also contemplated herein are compositions that may comprise components of various consistency as well as components that may include more than one consistency, for example, soft, chewy meat-like particles as well as kibble having an outer cereal component and an inner cream component as described in, e.g., U.S. Pat. No. 6,517,877. The kibble may then be dried and optionally coated with one or more topical coatings known by those skilled in the art, for example, flavors, fats, oils, powders, and the like.

In accordance with the present invention, compositions 1.0-2.15 can be administered to an animal to prevent or treat obesity in the animal, preferably without loss of lean muscle mass. Prevention of obesity may be accomplished by administering to an animal an effective amount of the compositions of the present invention over a period of time, monitoring the animal's weight adipose tissue, and lean muscle mass, and adjusting the amount of food fed to the animal to prevent the animal from gaining excess adipose tissue and preserve or cause a gain in lean muscle mass. Treatment of obesity may be accomplished by administering to an animal an effective amount of the compositions of the present invention and monitoring the animal's adipose tissue content until the animal has lost sufficient adipose tissue to be considered an ideal weight, as understood by one of skill in the art.

In accordance with the present invention, compositions 1-2.15 can be fed to an animal, not only to treat obesity without loss of lean muscle, but to cause gain of lean muscle in an animal in need thereof. Said animal need not be obese; gain of lean muscle may be desirable in animals whose lean muscle mass is less than ideal due to any number of factors including, e.g., age, disease, or malnutrition. Gain of lean muscle may be accomplished by administering to an animal an effective amount of the compositions of the present invention while monitoring the animal's lean muscle content until the animal has gained a sufficient amount of lean muscle to be considered an ideal weight, or sufficient as determined by one of skill in the art.

The compositions and methods of the present invention may be part of an overall weight loss program, for example, the compositions and methods may be used in combination with regular exercise and restricted access to treats, table scraps or other pet snacks.

The present invention also includes the use of any one of compositions 1.0-2.15 to prevent or treat obesity, and/or to preserve lean muscle, and/or to cause gain of lean muscle. The present invention also includes the use of any one of compositions 1.0-2.15 in the manufacture of a food composition, preferably a pet food composition, more preferably a dog food, to prevent or treat obesity, and/or to preserve lean muscle, and/or to cause gain of lean muscle.

EXAMPLES

Example 1

Formulation of Compositions

The following compositions of Table 1 are formulated in accordance with the Association of American Feed Control Officials 2005 nutrient guide for dogs, balanced to meet adult maintenance requirements, and extruded as a dry kibble. The contents of the compositions are analyzed by methods known in the art.

TABLE 1

|  | Control | Formula A | Formula B |
| --- | --- | --- | --- |
| Crude Protein, % | 28.34 | 33.87 | 33.42 |
| Crude Fat, % | 9.65 | 8.54 | 9.05 |
| Crude Fiber, % | 20.87 | 10.33 | 11.57 |
| Total Dietary Fiber, % | 33.54 | 25.4 | 25.39 |
| Soluble Fiber, % | 0.98 | 3.01 | 1.61 |
| Ash, % | 5.08 | 6.3 | 6.16 |
| Calcium, % | 0.79 | 0.93 | 0.93 |
| Phosphorous, % | 0.61 | 0.8 | 0.79 |
| Manganese, ppm | 30 | 100 | 100 |
| Lysine, % | 1.51 | 1.74 | 1.70 |
| Methionine, % | 0.50 | 1.23 | 1.24 |
| Methionine + Cysteine, % | 0.83 | 1.65 | 1.67 |
| Tryptophan, % | 0.28 | 0.27 | 0.24 |
| Threonine, % | 1.07 | 1.24 | 1.22 |
| Arginine, % | 1.55 | 1.64 | 1.71 |
| Isoleucine, % | 1.02 | 1.19 | 1.09 |
| Valine, % | 1.23 | 1.39 | 1.29 |
| Leucine, % | 2.21 | 3.82 | 3.74 |
| Histidine, % | 0.60 | 0.69 | 0.67 |
| Phenylalanine + Tyrosine, % | 1.81 | 2.91 | 2.92 |
| Carnitine (Added), ppm | 300 | 300 | 300 |
| Linolenic acid, % | 0.32 | 0.96 | 0.29 |
| Linoleic acid, % | 3.04 | 2.03 | 2.90 |
| Metabolizable Energy, kcal/kg | 2940 | 3283 | 3241 |
| Lysine: Calorie | 5.14 | 5.30 | 5.25 |
| Methionine + cysteine: Lysine | 0.55 | 0.95 | 0.98 |
| Tryptophan: Lysine | 0.19 | 0.16 | 0.14 |
| Threonine: Lysine | 0.71 | 0.71 | 0.72 |
| Arginine: Lysine | 1.03 | 0.94 | 1.01 |
| Isoleucine: Lysine | 0.68 | 0.68 | 0.64 |
| Valine: Lysine | 0.81 | 0.80 | 0.76 |
| Leucine: Lysine | 1.46 | 2.20 | 2.20 |
| Histidine: Lysine | 0.40 | 0.40 | 0.39 |
| Phenylalanine + Tyrosine: Lysine | 1.20 | 1.67 | 1.72 |

Example 2

Canine Weight Loss Study

Thirty obese dogs (beagles) are utilized in a 120 day weight loss study. All dogs have a percent body fat (total weight) of greater than 26%. The dogs are randomly divided into three groups, and fed either Control, Formula A, or Formula B. Dogs are fed amounts according to their ideal body weight, i.e., the number of kcal per day according to a dog's ideal body weight and is calculated as follows:

a dog's ideal body weight is calculated as:

$$W_1 = \frac{W_0 - W_0(F_0/100)}{(1 - F_1/100)}$$

wherein $W_1$=ideal weight (kg), $W_0$=initial weight (kg), $F_0$=measured body fat (%), and $F_1$=ideal body fat (%). Dogs utilized in the study are deemed to have an ideal body fat of 20%. The number of kcal fed per day according to a dog's ideal body weight is calculated as follows:

$1.6 \times (70 \cdot W_1)^{3/4}$=kcal/day fed to a dog according to its ideal body weight.

The amount of food fed per dog is determined by dividing the number of kcal per day for a dog according to ideal body weight by the number of kcal per kilogram of food, i.e., kcal/kg of Control, Formula A, and Formula B.

During the study, each dog undergoes DEXA scans (DXA-QDR-4500, Hologic, Inc., Waltham, Mass.) at days 0, 30, 60, 90, and 120 days to measure lean muscle, and body fat. At days 0 and 30, n=10 for dogs each fed Control, Formula A, and Formula B compositions. Dogs are removed from the study when they achieve less than 25% body fat. At day 60), 4 dogs fed Formula A and 2 dogs fed Formula B are removed from the study. Thus, for data at day 90:

n=10 for dogs fed Control;
n=6 for dogs fed Formula A; and
n=8 for dogs fed formula B.

At day 90, 2 dogs fed Control, 4 dogs fed Formula A and 3 dogs fed Formula B are removed from the study. Thus, for data at day 120:

n=8 for dogs fed Control;
n=7 for dogs fed Formula A; and
n=5 for dogs fed Formula B.

Results of the study are provided in the following tables:

TABLE 2

Total body mass of dogs

| Total Weight (g) | Control | Formula A | Formula B |
| --- | --- | --- | --- |
| Day 0 | 15866 ± 920 | 16645 ± 920 | 17686 ± 920 |
| Day 30 | 14797 ± 881 | 15114 ± 881 | 16180 ± 881 |
| Day 60 | 14598 ± 904 | 14539 ± 904 | 15739 ± 953 |
| Day 90 | 13815 ± 880 | 14820 ± 1136 | 16160 ± 984 |
| Day 120 | 13977 ± 1016 | 15729 ± 1659 | 15942 ± 1285 |
| Change day 0 to 30 | −1069 ± 262 | −1531 ± 262 | −1506 ± 262 |
| Change day 0 to 60 | −1268 ± 314 | −2105 ± 314 | −2166 ± 331 |
| change day 0 to 90 | −2051 ± 291 | −1809 ± 376 | −2347 ± 326 |
| Change day 0 to 120 | −2456 ± 349 | −1892 ± 570 | −2408 ± 441 |
| Day 0 vs day 30* | <0.01 | <0.01 | <0.01 |
| Day 0 vs day 60* | <0.01 | <0.01 | <0.01 |
| Day 0 vs day 90* | <0.01 | <0.01 | <0.01 |
| Day 0 vs day 120* | <0.01 | <0.01 | <0.01 |

*Probability of greater F value

TABLE 2A

Analysis of dog body mass change

| Total Weight (g) | Control vs. Formula A* | Control vs. Formula B* | Formula A vs Formula B* |
|---|---|---|---|
| Day 0 | ND | ND | ND |
| Day 30 | ND | ND | ND |
| Day 60 | ND | ND | ND |
| Day 90 | ND | ND | 0.09 |
| Day 120 | ND | ND | ND |
| Change day 0 to 30 | ND | ND | ND |
| Change day 0 to 60 | 0.07 | 0.06 | ND |
| Change day 0 to 90 | ND | ND | ND |
| Change day 0 to 120 | ND | ND | ND |

*Probability of greater F value, ND = No difference

TABLE 3

Lean muscle mass of dogs

| Muscle (g) | Control | Formula A | Formula B |
|---|---|---|---|
| Day 0 | 9840 ± 563 | 10161 ± 563 | 10864 ± 563 |
| Day 30 | 9266 ± 479 | 9775 ± 479 | 10389 ± 479 |
| Day 60 | 8713 ± 493 | 10502 ± 493 | 11250 ± 519 |
| Day 90 | 9452 ± 498 | 9843 ± 643 | 10997 ± 557 |
| Day 120 | 9183 ± 507 | 9520 ± 828 | 10368 ± 641 |
| Change day 0 to 30 g | −573 ± 159 | −386 ± 159 | −475 ± 159 |
| Change day 0 to 60, g | −1126 ± 155 | 341 ± 155 | 235 ± 163 |
| Change day 0 to 90, g | −387 ± 198 | −153 ± 256 | −284 ± 221 |
| Change day 0 to 120, g | −832 ± 255 | −748 ± 416 | −457 ± 323 |
| Day 0 vs Day 30* | <0.01 | 0.02 | <0.01 |
| Day 0 vs day 60* | <0.01 | 0.04 | ND |
| Day 0 vs day 90* | 0.06 | ND | ND |
| Day 0 vs day 120* | <0.01 | ND | ND |

*Probability of greater F value,
ND = No difference

TABLE 3A

Analysis of dog muscle mass change

| Muscle (g) | Control vs Formula A* | Control vs Formula B* | Formula A vs Formula B* |
|---|---|---|---|
| Day 0 | ND | ND | ND |
| Day 30 | ND | ND | ND |
| Day 60 | 0.02 | <0.01 | ND |
| Day 90 | ND | 0.05 | ND |
| Day 120 | ND | ND | ND |
| Change day 0 to 30 g | ND | ND | ND |
| Change day 0 to 60, g | <0.01 | <0.01 | ND |
| Change day 0 to 90, g | ND | ND | ND |
| Change day 0 to 120, g | ND | ND | ND |

*Probability of greater F value, ND = NO difference

TABLE 4

Fat mass of dogs

| Fat (g) | Control | Formula A | Formula B |
|---|---|---|---|
| Day 0 | 5602 ± 446 | 5997 ± 446 | 6321 ± 446 |
| Day 30 | 5128 ± 503 | 4876 ± 503 | 5315 ± 503 |
| Day 60 | 5491 ± 528 | 3571 ± 528 | 4005 ± 557 |
| Day 90 | 3964 ± 521 | 4520 ± 673 | 4680 ± 583 |
| Day 120 | 4395 ± 608 | 5761 ± 993 | 5103 ± 769 |
| Change day 0 to 30 | −474 ± 212 | −1121 ± 212 | −1006 ± 212 |
| Change day 0 to 60 | −111 ± 284 | −2426 ± 284 | −2374 ± 799 |
| Chance day 0 to 90 | −1638 ± 211 | −1632 ± 273 | −2021 ± 236 |
| Change day 0 to 120 | −1592 ± 249 | −1104 ± 407 | −1899 ± 315 |

TABLE 4-continued

Fat mass of dogs

| Fat (g) | Control | Formula A | Formula B |
|---|---|---|---|
| Day 0 vs day 30* | 0.03 | <0.01 | <0.01 |
| Day 0 vs day 60* | ND | <0.01 | <0.01 |
| Day 0 vs day 90* | <0.01 | <0.01 | <0.01 |
| Day 0 vs day 120* | <0.01 | 0.02 | <0.01 |

*Probability of greater F value,
ND = No difference

TABLE 4A

Analysis of fat mass change

| Fat (g) | Control vs Formula A* | Control vs Formula B* | Formula A vs Formula B* |
|---|---|---|---|
| Day 0 | ND | ND | ND |
| Day 30 | ND | ND | ND |
| Day 60 | 0.02 | 0.06 | ND |
| Day 90 | ND | ND | ND |
| Day 120 | ND | ND | ND |
| Change day 0 to 30 | 0.04 | 0.09 | ND |
| Change day 0 to 60 | <0.01 | <0.01 | ND |
| Change day 0 to 90 | ND | ND | ND |
| Change day 0 to 120 | ND | ND | ND |

*Probability of greater F value, ND = No difference

The results indicate that although all animals lose lean muscle in the first 30 days of the study, animals fed Formulas A and B statistically lose more adipose tissue than animals fed Control. The results also indicate that at day 60, animals fed Formulas A and B regain lean muscle (compared with Control).

Example 3

Formulation of Compositions

Compositions are formulated in accordance with the specifications of Table 5 on a dry matter basis:

TABLE 5

| | Minimum | Target | Maximum |
|---|---|---|---|
| Protein % | 33 | 35 | 36 |
| Soluble Fiber % | 1.2 | | 4 |
| Insoluble Fiber % | 23 | | 25 |
| Dietary Fiber % | 24 | | 27 |
| Lysine:energy (g/Mcal) | 5.7 | | |
| Leucine:Lysine ratio | | 2 | |
| Methionine % | 1.4 | | 1.5 |
| Manganese (ppm) | | 100 | |
| Carnitine (ppm) | 300 | | 350 |

Example 4

Formulation of Dry Composition

The composition of Example 3 is formulated as a dry dog food having a metabolizable energy content of about 3100 kcal/kg.

Example 5

Formulation of Wet Composition

The composition of Example 3 is formulated as a wet dog food having a metabolizable energy content of about 900 kcal/kg on a wet matter basis.

While particular embodiments of the present invention have been shown and described herein, it will be apparent to those skilled in the art that changes and modifications may be made without departing from the broader aspects of invention.

What is claimed is:

1. A method to treat obesity in an animal without concomitant loss of lean muscle mass comprising administering to said animal a composition comprising about 1.4 to about 2.1% lysine, wherein the composition has
   a leucine to lysine ratio of about 1.7 to about 2.7,
   a methionine+cysteine to lysine ratio of about 0.5 to about 1.5,
   a phenylalanine+tyrosine to lysine ratio of about 1.3 to about 2.1,
   about 4 to about 8 grams of lysine per Mcal, and
   about 20 to about 30% dietary fiber.

2. A method for the preservation of lean muscle mass in an animal comprising administering to the animal a composition comprising about 1.4 to about 2.1% lysine, wherein the composition has
   a leucine to lysine ratio of about 1.7 to about 2.7,
   a methionine+cysteine to lysine ratio of about 0.5 to about 1.5,
   a phenylalanine+tyrosine to lysine ratio of about 1.3 to about 2.1,
   about 4 to about 8 grams of lysine per Mcal, and
   about 20 to about 30% dietary fiber.

3. A method for the gain of lean muscle mass in an animal comprising administering to said animal a composition comprising about 1.4 to about 2.1% lysine, wherein the composition has
   a leucine to lysine ratio of about 1.7 to about 2.7,
   a methionine+cysteine to lysine ratio of about 0.5 to about 1.5,
   a phenylalanine+tyrosine to lysine ratio of about 1.3 to about 2.1,
   about 4 to about 8 grams of lysine per Mcal, and
   about 20 to about 30% dietary fiber.

4. The method of claim 1 wherein the animal is a companion animal.

5. The method of claim 4 wherein the companion animal is a dog.

6. The method of claim 1, wherein the composition comprises about 8 to about 14% crude fiber.

7. The method of claim 1, wherein the composition comprises about 1.2 to about 4.0% soluble fiber.

8. The method of claim 1, wherein the composition has about 4.2 to about 6.8 grams of lysine per Mcal.

9. The method of claim 1, wherein the composition has about 1.5% to about 1.9% lysine.

10. The method of claim 1, wherein the composition has a leucine to lysine ratio of about 2.0 to about 2.4.

11. The method of claim 1, wherein the composition has a methionine+cysteine to lysine ratio of about 0.8 to about 1.2.

12. The method of claim 1, wherein the composition has a phenylalanine+tyrosine to lysine ratio of about 1.5 to about 1.9.

13. The method of claim 1, wherein the composition has a tryptophan to lysine ratio of about 0.1 to about 0.2.

14. The method of claim 1, wherein the composition has a threonine to lysine ratio of about 0.5 to about 0.9.

15. The method of claim 1, wherein the composition has an arginine to lysine ratio of about 0.75 to about 1.2.

16. The method of claim 1, wherein the composition has an isoleucine to lysine ratio of about 0.51 to about 0.82.

17. The method of claim 1, wherein the composition has a valine to lysine ratio of about 0.6 to about 1.0.

18. The method of claim 1, wherein the composition has a histidine to lysine ratio of about 0.3 to about 0.5.

19. The method of claim 1, wherein the composition has a methionine to lysine ratio of about 0.5 to about 0.9.

20. The method of claim 1, wherein the composition has a metabolizable energy content of about 2600 to about 3950 Kcal/kg.

21. The method of claim 1, wherein the composition further comprises about 75 to about 200 ppm manganese.

22. The method of claim 1, wherein the composition further comprises about 200 to about 500 ppm L-carnitine.

23. The method of claim 1, wherein the composition further comprises about 24 to about 41% crude protein.

* * * * *